United States Patent [19]
Koji

[11] Patent Number: 4,742,235
[45] Date of Patent: May 3, 1988

[54] OPTICAL TREATMENT DEVICE

[75] Inventor: Masashi Koji, Tokyo, Japan

[73] Assignees: Hoshin Kagaku Sangyosho Co., Ltd.; Photon Co., Ltd., both of Tokyo, Japan

[21] Appl. No.: 885,246

[22] Filed: Jul. 14, 1986

[30] Foreign Application Priority Data

Jul. 18, 1985 [JP] Japan .................... 60-109960[U]

[51] Int. Cl.⁴ .................................................. G01J 1/00
[52] U.S. Cl. ............................. 250/504 R; 128/395
[58] Field of Search .............. 250/492.1, 493.1, 494.1, 250/504 R, 503; 128/379, 402, 907, 395; 219/121 L, 121 LM

[56] References Cited

U.S. PATENT DOCUMENTS

| | | | |
|---|---|---|---|
| 1,589,338 | 6/1926 | White | 250/504 |
| 2,773,531 | 12/1956 | Johnson | 128/402 |
| 3,316,405 | 4/1967 | Astheimer | 250/504 |
| 4,042,803 | 8/1977 | Bickford | 128/379 |
| 4,044,756 | 8/1977 | Hamilton et al. | 128/395 |
| 4,249,533 | 2/1981 | Komiya | 128/395 |
| 4,470,417 | 9/1984 | Gruber | 128/402 |
| 4,535,784 | 8/1985 | Rohlicek et al. | 128/907 |
| 4,558,698 | 12/1985 | O'Dell | 128/395 |

FOREIGN PATENT DOCUMENTS 2740969 3/1979 Fed. Rep. of Germany ...... 128/907

*Primary Examiner*—Bruce C. Anderson
*Attorney, Agent, or Firm*—Murray Schaffer

[57] ABSTRACT

An optical treatment device having a light emission element, a power source for supplying a power to the light emission element and an attaching member for attaching the light emission element to an arbitrary portion such that a light emission face of the light emission element faces a desired portion to be irradiated, whereby the light emission element can be detachably attached to the arbitrary portion and a light such as infrared rays, a laser light and so on can irradiate or heat a very small area of the desired portion.

17 Claims, 2 Drawing Sheets

OPTICAL TREATMENT DEVICE

BACKGROUND OF THE INVENTION

1. Field of the Invention

The present invention relates generally to optical treatment devices and, more particularly, is directed to an optical treatment device which is attached to a so-called effective spot of a human body and the like so as to irradiate the effective spot with a light such as infrared rays and so on, thus treating the affected part of the human body.

2. Description of the Prior Art

As is well known, with respect to the muscular pains caused by blow, sprain and the like, such muscular pains are allayed by irradiating the affected part with infrared rays from an infrared lamp or quickening the circulation of the blood to thereby help the increase of the natural healing or recovering power.

A prior art infrared lamp generally irradiates a relatively large area of the human body so that the infrared lamp necessarily becomes large in size, consuming a large power. Accordingly, when a very small area of the human body is irradiated with the infrared rays, if an optical mask is used, it becomes possible to irradiate the very small area of the human body with the infrared rays from the infrared lamp. In this case, there arise problems that a large power is consumed by the infrared lamp and that a patient (user) can not move at all when he is irradiated with the infrared rays.

OBJECTS AND SUMMARY OF THE INVENTION

Accordingly, it is an object of this invention to provide an improved optical treatment device which can remove the defects encountered with the prior art infrared lamp.

It is another object of this invention to provide an optical treatment device in which a light emission element can be attached to a desired portion of a human body and a light such as infrared rays, a laser light can effectively irradiate or heat the desired portion very small in area, thus treating the affected part of the human body.

It is further object of this invention to provide an optical treatment device for portable use which is small in power consumption.

It is still further object of this invention to provide an optical treatment device of portable use which can enable the user to move and even to take a light exercise upon use.

According to one aspect of the present invention, there is provided an optical treatment device comprising:

a light emission element;

a power source for supplying a power to said light emission element; and attaching means for attaching said light emission element to an arbitrary portion such that a light emission face of said light emission element faces a desired portion to be irradiated.

According to another aspect of the present invention, there is provided an optical treatment device comprising:

a light emission element;

a power source for supplying a power to said light emission element so that said light emission element emits a light;

a cap member for holding said light emission element; and attaching means provided on said cap member and for fixing said cap member to a predetermined portion in such a manner that said light emitted from said light emission element is introduced to a desired portion.

These and other objects, features and adavantages of the present invention will become apparent from the following detailed description of the preferred embodiments taken in conjunction with the accompanying drawings, throughout which like reference numerals designate like elements and parts.

DESCRIPTION OF THE PREFERRED EMBODIMENTS

Figure 1:
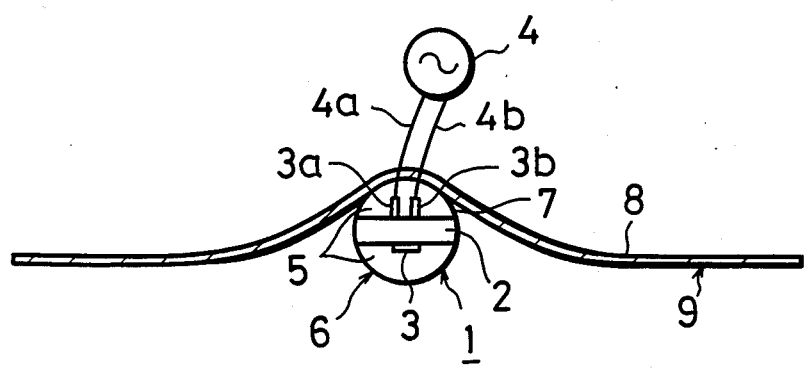
FIG. 1 is a cross-sectional view of an embodiment of an optical treatment device according to the present invention.

Referring now to the attached drawings, the present invention will hereinafter be described in detail. Throughout the following descriptions, like reference numerals designate like elements and parts.

FIG. 1 is a cross-sectional view illustrating a first embodiment of an optical treatment device according to this invention.

In FIG. 1, reference numeral 1 generally designates a light emission element. This light emission element 1 is formed such that a chip 3 made of a semiconductor material such as an LED (light emission diode) for emitting infrared rays, a laser light or the like is formed on a substrate 2, pins 3a, 3b are led out from the semiconductor chip 3 through the substrate 2 to the opposing side of the chip 3, these pins 3a, 3b are respectively connected with lead wires 4a, 4b which are connected to a power source 4, and the substrate 2, the chip 3 and the like are housed in a housing member 5 made of resinous material to be of substantially spherical shape by the coating. In this embodiment, the light emission element 1 emits, for example, infrared rays by supplying a power to the chip 3 via the lead wires 4a, 4b and the pins 3a, 3b from the power source 4.

An adhesive tape 8 is attached to the light emission element 1 at its rear surface 7 which is located at the opposite side of a light emission face 6 at which side the chip 3 is provided. In this case, a coating surface 9 on which the adhesive agent of the adhesive tape 8 is coated is faced to the side of the light emission element 1 and the light emission element 1 is bonded to the adhesive tape 8 by this adhesive agent. It is possible that the shape of the adhesive tape 8 is selected circular, rectangular and others.

According to the optical treatment device thus constructed, the light emission face 6 of the light emission element 1 is abutted against the part requiring the treatment, for example, the so-called effective spot for the treatment of, for example, a human body and the adhesive tape 8 is bonded to its skin, whereby this light emission element 1 is fixedly attached to the desired part of the human body.

Under the state that the light emission element 1 is fixedly attached to the desired part of the human body, when a current is supplied from the power source 4, such as the commercially available power source, the battery or the like to the chip 3 of the light emission element 1 via the lead wires 4a, 4b and the pins 3a, 3b, the infrared rays, for example, are emitted from the chip 3 and penetrated into the skin, heating the affected part, which is then healed. At that time, since the light emission element 1 is fixed to the human body by the adhesive tape 8, if the patient moves or takes a proper bodily exercise during a period in which the optical treatment device is being powered, there will arise no trouble.

Figure 2:
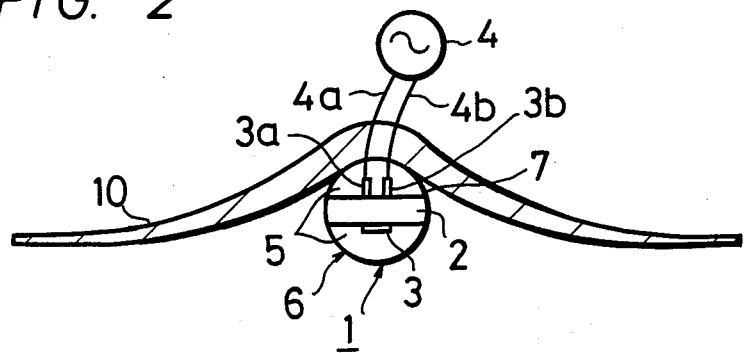
FIG. 2 is a cross-sectional view of a second embodiment of the present invention.

FIG. 2 is a like cross-sectional view illustrating a second embodiment of the optical treatment device according to this invention. In this embodiment, instead of the adhesive tape 8 (in FIG. 1), a so-called sucking disc 10 made of, for example, rubber is bonded to the rear surface 7 of the like light emission element 1. According to the second embodiment, the light emission face 6 of the light emission element 1 is held on the necessary portion (affected part) of the human body and then the sucking disk 10 is pressed against the skin, thus the optical treatment device of this embodiment being fixed to the affected part. When the sucking disk 10 is used, if the inner surface of the sucking disk 10 is watered, the optical treatment device can be fixed to the human body more easily and positively.

Figure 3:
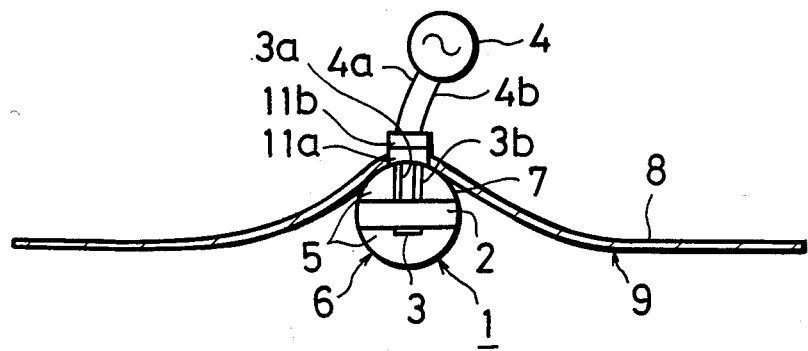
FIG. 3 is a cross-sectional view of a third embodiment of the present invention.

FIG. 3 is a like cross-sectional view illustrating a third embodiment of the optical treatment device according to this invention. The third embodiment is a version of the first embodiment shown in FIG. 1, in which connectors 11a and 11b, which can be electrically and mechanically coupled to or detached from each other, are provided on the rear surface 7 of the light emission element 1. That is, one connector 11b is connected with the lead wires 4a, 4b and the other connector 11a is connected with the pins 3a, 3b. According to this embodiment, the exchange of the light emission element 1 mounted on the tip end of the long lead wires 4a and 4b becomes easy.

Figure 4:
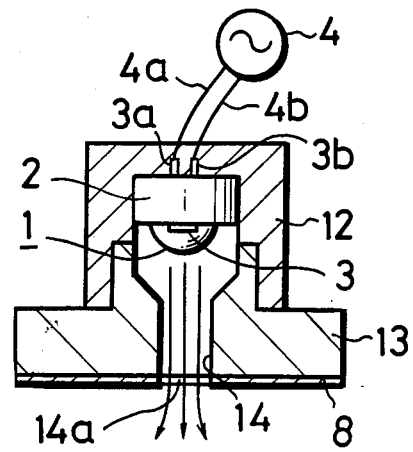
FIG. 4 is a cross-sectional view of a fourth embodiment of the present invention.

FIG. 4 is a cross-sectional view of a fourth embodiment of the optical treatment device according to this invention. In this embodiment, the light emission element 1 is fixed to a bottom portion of a cap member 12 made of, for example, a resinous material and the like and the open end portion of this cap member 12 is engaged with an annular-shaped support base or pad 13 made of, for example, a resinous material and which acts as a heat insulating material. The adhesive tape 8 whose one portion corresponding to an irradiation opening 14 formed through the support base 13 is removed and hence which is formed as an annular-shaped form, is bonded to the lower surface or the free end surface of the support base 13.

According to the fourth embodiment of the invention, when it is fixed by the adhesive tape 8 to a desired portion and the light emission element is excited, the infrared rays, for example, emitted from the light emission element 1 are traveled through the irradiation opening 14, which is bored through the central portion of the support base 13, to the outside as shown by arrows so as to irradiate or heat the desired portion.

If a reflection plate 14a is mounted on the surface of the opening 14 or the surface of the opening 14 is plated with metal as shown by reference numeral 14a, it becomes possible to more effectively utilize the light emitted from the light emission element 1.

Further, if the diameter of the opening 14 is reduced, it becomes possible to arrange the light emitted from the light emission element 1 as a beam-shaped light.

Furthermore, the support base 13 may be made of either transparent material or colored material. When the light emitted from the light emission element 1 is the invisible light, such as the infrared rays and so on, if the support base 13 is made of a resinous material which is colored when it receives the infrared rays, the user can visually check whether or not the light emission element 1 emits the light.

Figure 5:
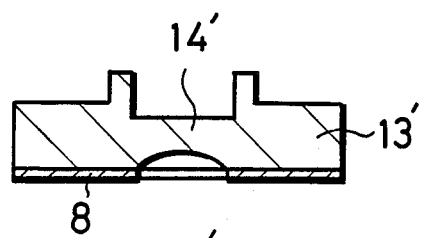
FIG. 5 is a cross-sectional view of a fifth embodiment of the present invention.

FIG. 5 is a cross-sectional view showing a support base 13' of a fifth embodiment of the invention. In this embodiment, the support base 13' is made of a resinous material which can pass therethrough the light emitted from the light emission element 1 so that it is not necessary to provide the opening 14 in the support base 13' unlike the fourth embodiment shown in FIG. 4. In this case, the adhesive tape 8 is arranged as an annular-shape similarly to that in the fourth embodiment shown in FIG. 4. In this embodiment, a portion 14' corresponding to the opening 14 in the fourth embodiment shown in FIG. 4 is arranged as a portion having a concavity or convexity so as to achieve a concave or convex lens effect, whereby the light emitted from the light emission element 1 can be diverged or converged. In this case, the other portions including the light emission element 1 and so on are substantially same as those shown in FIG. 4.

Figure 6:
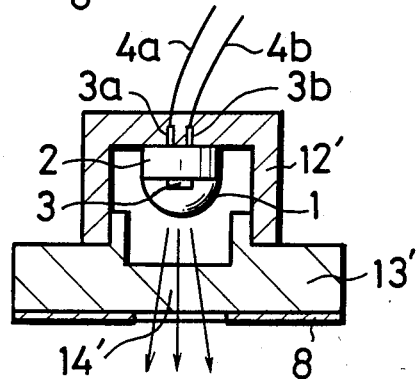
FIG. 6 is a cross-sectional view of a sixth embodiment of the present invention.

FIG. 6 is a cross-sectional view illustrating a sixth embodiment of the invention. In this embodiment, while the support base 13' is formed the same as that in the fifth embodiment shown in FIG. 5, a cap member 12' having the light emission element 1 is made of a resinous material which can be colored when the cap member 12' receives the light emitted from the light emission element 1. Accordingly, the user can confirm from the side of the cap member 12' whether or not the light is emitted from the light emission element 1.

Figure 7:
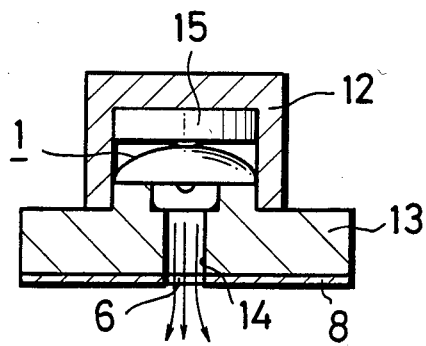
FIG. 7 is a cross-sectional view of a seventh embodiment of the present invention.

FIG. 7 is a cross-sectional view illustrating a seventh embodiment of the invention. In the illustrated embodiment, a thin dry cell 15, such as a mercury oxide cell and the like is fixed to the bottom portion of the cap member 12 as the power source of the light emission element 1, the light emission element 1 is engaged into the opening end portion of the cap member 12 such that when the cap member 12 is engaged into the support base 13 and the light emission surface 6 of the light emission element 1 opposes the opening 14 of the support base 13, in order that the light emission element 1 and the dry cell 15 are electrically contacted with each other automatically and an electric power is supplied from the latter to the former, though not shown, the electrodes of the dry cell 15 and terminal pins of the light emission element 1 are provided. According to this embodiment, since the optical treament device itself includes the power source which is assembled as a unitary body, there can be achieved great effects in practical use.

In the embodiment shown in FIG. 7, if the dry cell is formed of a solar battery and placed at the outside of the upper portion of, for example, the cap member 12, so long as it is used properly, the dry cell can be used in a semi-permanent fashion.

While in the embodiments shown in FIGS. 4 to 7 the adhesive tape bonded to the lower surface of the support base is arranged as the annular-shape as seen from the under side, if the adhesive tape can pass therethrough the light emitted from the light emission element and the adhesive force of the adhesive tape can be prevented from being weakened by such a light, it is possible to bond the adhesive tape to the whole surface of the lower surface of the support base.

Further, when the adhesive tape bonded to the support base loses its adhesive force, if the useless adhesive tape is replaced, it is possible to use the optical treatment device again.

Furthermore, while throughout the embodiments shown in FIGS. 4 to 7 the cap member and the support base are formed separately, it is possible to form the cap member and the support base as a unitary body.

In this case, in order to prevent the life of the chip 3 to emit the light from being shortened by the heat generated in the chip 3 itself, it is possible that the cap member 12 holding the chip 3 be made of materials, such as metals, ceramics and the like whose thermal conductivity is excellent to thereby effectively radiate the heat outside the chip 3.

Further, if the chip 3 is continuously operated to emit a light, the chip 3 is lowered in, for example, light emission ratio. To avoid this defect, it is possible to provide an intermittent switch between the power source 4 and the chip 3, whereby a power is intermittently supplied to the chip 3.

When the temperature of the heat generated in the chip 3 does not reach so high temperature, the support base 13 or 13' may be omitted and the adhesive tape 8 may be directly bonded to the lower surface of the cap member 12.

Further, an adhesive tape on both surfaces of which adhesive agent is coated can be used as the adhesive tape of the embodiments shown in FIGS. 4 to 7.

The above description is given on the preferred embodiments of the invention but it will be apparent that many modifications and variations could be effected by one skilled in the art without departing from the spirits or scope of the novel concepts of the invention so that the scope of the invention should be determined by the appended claims only.

I claim as my invention:

1. An optical treatment device comprising:
   a generally opaque housing of lightweight and portability capable of being supported on a limb or body portion of the user, said housing having a light transmissive passage extending outwardly therefrom,
   a light emission element located in said housing having a face aligned with said passage and through which light radiation is emitted,
   a source of current for supplying power to said light emission element and means for attaching said housing directly to the body of the user adjacent the area of the body selected for treatment such that the radiation emitted from face of said light emission element passes through said passage directly onto the skin of the user solely within the selected area of the body.

2. An optical treatment device according to claim 1, in which said means for attaching said housing is provided on the rear surface of said housing opposing the opening therein, and includes bonding means by which said light emission face of said light emission element closely contacts the selected area of the body.

3. An optical treatment device according to claim 2, in which said bonding means is an adhesive tape.

4. An optical treatment device according to claim 2, in which said bonding means is a suction pad.

5. An optical treatment device according to claim 1 in which said light emission element comprises a substrate, a semiconductor light emission element formed on said substrate.

6. An optical treatment device according to claim 5, further comprising a connector for electrically or mechanically coupling or detaching said light emission element and said power source.

7. An optical treatment device according to 1 in which said light emission element emits infrared rays.

8. An optical treatment device comprising:
   a housing having a base formed with a light transmissive passage therein and a cap aligned with said passage and closing the same at one end, said housing being light in weight and portable,
   a light emitting element for generating an irradiating light and having a face through which said irradiating light is emitted, said light emitting element being mounted in said cap so that said face is aligned with the passage in said base to permit the light to exit therefrom,
   a source of current for supplying power to said light emission element and means for attaching said housing directly to the body of the user adjacent the area of the body selected for treatment such that the radiation emitted from face of said light emission element passes through said passage directly onto the skin of the user solely within the selected area of the body.

9. An optical treatment device according to claim 8, wherein the support base is fixedly engaged with said cap and said attaching means is fixed to its free surface of said support base.

10. An optical treatment device according to claim 9, in which said cap member and said support base are made of resinous material.

11. An optical treatment device according to claim 9, in which said light transmission passage of said support base is an opening.

12. An optical treatment device according to claim 11, in which said support base is provided on a surface of said opening with reflecting means.

13. An optical treatment device according to claim 9, in which said light transmission passage of said support base includes a concave lens.

14. An optical treatment device according to claim 9, in which said light transmission passage of said support base includes a convex lens.

15. An optical treatment device according to claim 9, in which said support base is made of the resinous material which is colored when it receives a light from said light emission element 16. An optical treatment device according to claim 8, in which said cap member is made of a resinous material which is colored when it receives the light from said light emission element.

17. An optical treatment device according to claim 9, in which said cap member houses a dry cell as said power source for supplying a power to said light emission element and said dry cell supplies a power automatically to said light emission element when said cap member is engaged with said support base.

* * * * *